United States Patent
Costanzo

(10) Patent No.: US 10,049,787 B2
(45) Date of Patent: Aug. 14, 2018

(54) INTERNALLY SEALABLE WIRE

(71) Applicant: Covidien LP, Mansfield, MA (US)

(72) Inventor: Joseph Costanzo, Hatfield, PA (US)

(73) Assignee: Covidien LP, Mansfield, MA (US)

( * ) Notice: Subject to any disclaimer, the term of this patent is extended or adjusted under 35 U.S.C. 154(b) by 921 days.

(21) Appl. No.: 14/452,911

(22) Filed: Aug. 6, 2014

(65) Prior Publication Data

US 2015/0112317 A1    Apr. 23, 2015

Related U.S. Application Data

(60) Provisional application No. 61/892,665, filed on Oct. 18, 2013.

(51) Int. Cl.
| | | |
|---|---|---|
| H01B 7/285 | (2006.01) | |
| H01B 7/24 | (2006.01) | |
| A61B 17/00 | (2006.01) | |
| H01B 7/36 | (2006.01) | |
| H01B 7/282 | (2006.01) | |
| A61B 17/072 | (2006.01) | |
| A61B 17/16 | (2006.01) | |
| A61B 90/00 | (2016.01) | |

(52) U.S. Cl.
CPC .............. *H01B 7/285* (2013.01); *A61B 17/00* (2013.01); *H01B 7/282* (2013.01); *A61B 17/07207* (2013.01); *A61B 17/1613* (2013.01); *A61B 17/1622* (2013.01); *A61B 2017/00398* (2013.01); *A61B 2017/00734* (2013.01); *A61B 2090/0813* (2016.02)

(58) Field of Classification Search
CPC ........ H01B 7/282; H01B 7/285; A61B 17/00; A61B 2017/2948; A61B 17/07207; A61B 177/1613; A61B 2017/00398; A61B 2017/00734; A61B 17/1622; A61B 2090/0813

USPC ................................ 604/95.04, 95.01, 95.05

See application file for complete search history.

(56) References Cited

U.S. PATENT DOCUMENTS

| | | |
|---|---|---|
| 3,347,974 A | 10/1967 | Ilse et al. |
| 4,095,039 A | 6/1978 | Thompson |
| 4,703,132 A | 10/1987 | Marciano-Agostinelli et al. |
| 5,281,757 A | 1/1994 | Marin et al. |
| 2013/0096498 A1* | 4/2013 | Baur ...................... A61B 17/29 604/95.04 |

(Continued)

OTHER PUBLICATIONS

European Office Action corresponding to counterpart Int'l Appln. No. EP 14 18 9362.8 dated Sep. 12, 2016.

(Continued)

*Primary Examiner* — Scott T Luan

(57) ABSTRACT

An internally sealable wire includes an elongate flexible body having a length and a plurality of electrically conductive strands disposed within an insulation jacket. The body includes an unsealed portion extending along a majority of the length of the body and at least one sealed portion positioned at a point along the length of the body. The unsealed portion includes open internal spaces defined between the strands and the insulation jacket, and the at least one sealed portion includes a filler material disposed within the internal spaces to effect a seal within the body and prevent the passage of fluid through the wire.

20 Claims, 3 Drawing Sheets

(56) References Cited

U.S. PATENT DOCUMENTS

2014/0200610 A1\* 7/2014 Igov .................. A61B 17/2909
606/205

OTHER PUBLICATIONS

European Search Report corresponding to EP 14 18 9362.8, completed Mar. 26, 2015 and dated Apr. 2, 2015; (8 pp).
Australian Examination Report No. 1 corresponding to counterpart Patent Appln. No. AU 201413573 dated Mar. 1, 2018.

\* cited by examiner

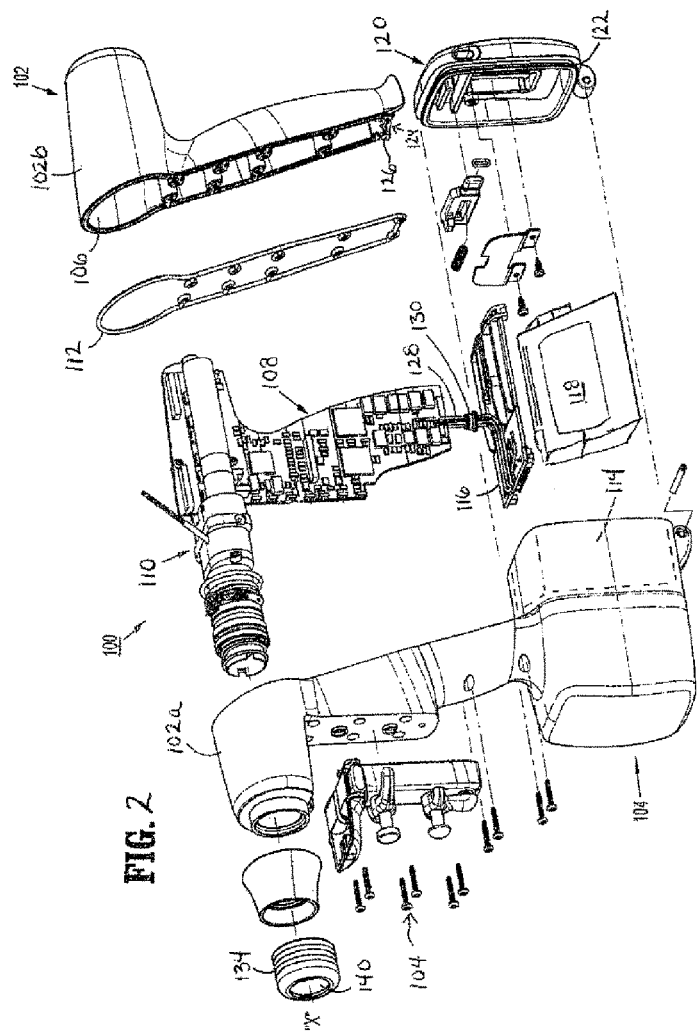
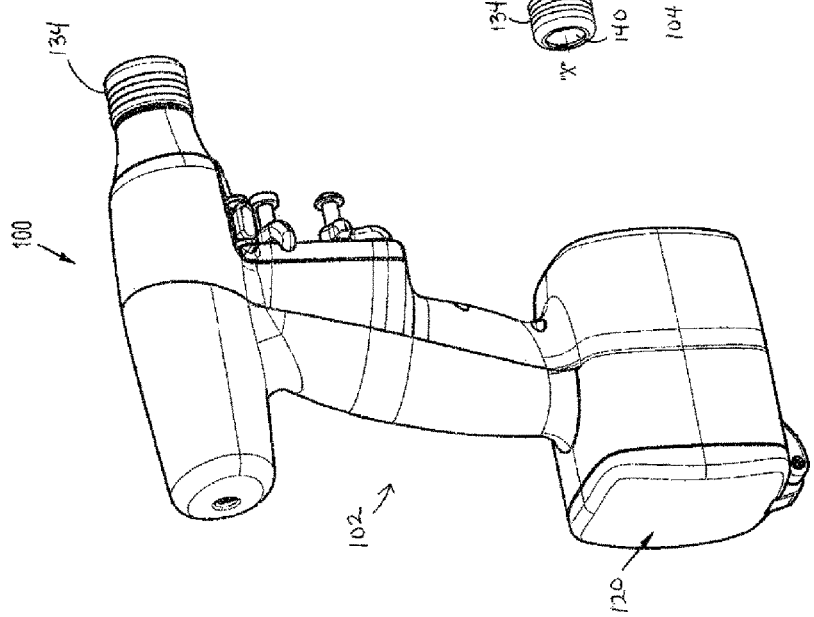

INTERNALLY SEALABLE WIRE

CROSS-REFERENCE TO RELATED APPLICATIONS

This application claims the benefit of and priority to U.S. Provisional Patent Application No. 61/892,665, filed Oct. 18, 2013, the entire disclosure of which is incorporated by reference herein.

BACKGROUND

1. Technical Field

The present disclosure relates generally to sealing electrical wires, and more particularly to wires that are internally sealable by displacement of an outer insulation jacket.

2. Background of Related Art

Autoclavable surgical devices often require appropriate sealing of internal electrical components (e.g., circuit boards, motors, batteries, etc.) from the outside environment while simultaneously requiring passage of electrical power and signals through connectors (e.g., bulkhead connectors) that provide the sealing. Traditionally, a stranded electrical wire is passed through a grommet, and the grommet seals an opening in the bulkhead connector. However, testing has revealed that the spaces between the individual strands of a stranded wire can provide a path for the passageway of gases, liquids, and vacuum through what is otherwise desired to be a sealed bulkhead connection. Moreover, due to space limitations, bulkhead connectors are often an impractical means of providing power and signal access.

SUMMARY

Internally sealable wires disclosed herein supplement or replace the sealing provided by a bulkhead connector by preventing the passage of fluid into/onto internal electrical components of a surgical device through the wires. In one aspect, an internally sealable wire may be passed through a bulkhead connector without the risk of losing the seal via the internal spaces defined between the individual strands of the stranded wire. In another aspect of the present disclosure, the bulkhead connector can be eliminated, which in turn may permit tighter packaging of the electrical components and thus, an overall smaller device.

An internally sealable wire in accordance with an embodiment of the present disclosure includes an elongate flexible body having a length and a plurality of electrically conductive strands disposed within an insulation jacket. The body includes an unsealed portion extending along a majority of the length of the body and at least one sealable portion positioned at a point along the length of the body. The unsealed portion includes open internal spaces defined between the strands and the insulation jacket, and the at least one sealable portion, when sealed, includes a filler material disposed within the internal spaces to effect a seal within the body and prevent the passage of fluid therethrough.

The at least one sealable portion may include at least two sealable portions. In some embodiments, the at least two sealable portions are disposed at first and second ends, respectively, of the body.

In some embodiments, the filler material disposed within the internal spaces of the sealed portion is displaced material of the insulation jacket. In other embodiments, the filler material is a sealant. In certain embodiments, the sealant is a hydrogel, and in certain other embodiments, the sealant is a foam.

In embodiments, an outer surface of the insulation jacket includes a visual indicator to differentiate between the unsealed and sealed portions of the wire.

The insulation jacket may include a strain relief. In some embodiments, the sealed portion is positioned between two points of the strain relief.

A surgical instrument in accordance with the present disclosure includes a housing including a wire having a first end connected to a first electrical component and a second end connected to a second electrical component. The wire includes an elongate flexible body including an insulation jacket and a plurality of electrically conductive strands disposed within the insulation jacket. Internal spaces defined between the insulation jacket and the strands are filled with a filler material at a sealed portion of the body.

A majority of the length of the wire may be an unsealed portion in which the internal spaces remain open.

In embodiments, the wire extends through a gasket and the sealable or sealed portion is positioned within the gasket.

The wire may include at least two sealed portions. In some embodiments, the at least two sealed portions are disposed at first and second ends, respectively, of the wire. In certain embodiments, at least one of the first and second ends of the wire is disposed within a connector. In certain other embodiments, at least one of the first and second ends of the wire is free of a connector and is in direct contact with its respective first or second electrical component.

In some embodiments, the filler material disposed within the internal spaces of the sealed portion is displaced material of the insulation jacket. In other embodiments, the filler material is a sealant. In certain embodiments, the sealant is a hydrogel, and in certain other embodiments, the sealant is a foam.

In embodiments, an outer surface of the insulation jacket includes a visual indicator to differentiate between the unsealed and sealed portions of the wire.

The insulation jacket may include a strain relief. In some embodiments, the sealed portion is positioned between two points of the strain relief.

BRIEF DESCRIPTION OF THE DRAWINGS

FIG. 1 is a perspective view of a surgical device in accordance with an embodiment of the present disclosure;

FIG. 2 is a perspective view, with parts separated, of the surgical device of FIG. 1;

DETAILED DESCRIPTION

Figure 3B:
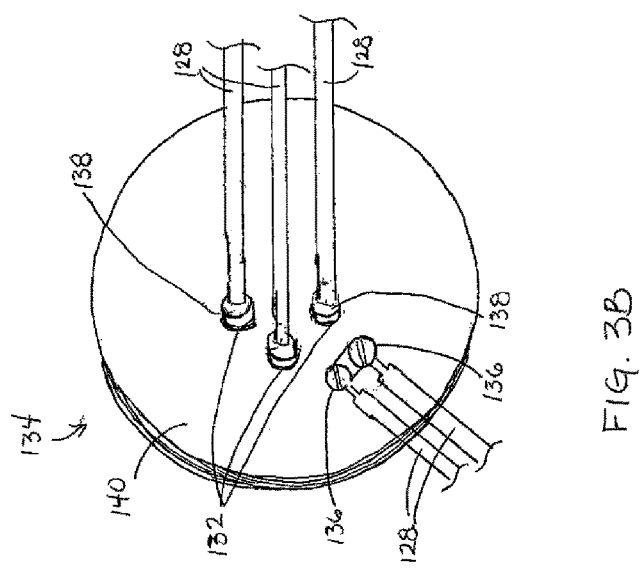
FIGS. 3A and 3B are perspective views of the front and the back of a connecting portion of the surgical device of FIG. 1.

The following discussion includes a description of internally sealed wires and surgical devices in which the internally sealed wires may be utilized. Embodiments of the presently disclosed wires are described in detail with reference to the drawings, in which like reference numerals designate identical or corresponding elements in each of the several views. In the following discussion, the term "proximal" or "trailing" will refer to the portion of a structure closer to a user, while the term "distal" or "leading" will refer to the portion further from the user.

A surgical device, in accordance with an embodiment of the present disclosure, is in the form of a powered hand held electromechanical instrument configured for selective attachment thereto of a plurality of adapters and/or end effectors (e.g., clamping jaws, cutting tools, staplers, etc.) that are each configured for actuation and manipulation by the powered hand held electromechanical surgical instrument. It should be understood, however, that the presently disclosed wires may be utilized in any surgical device that requires the sealed passage of wires between electrical components disposed within the surgical device, such as wires passed through an otherwise sealed bulkhead connector.

Referring now to FIGS. 1 and 2, a surgical device 100 includes a housing 102 having a distal section 102a and a proximal section 102b that are connected by a plurality of fasteners 104. The distal and proximal sections 102a, 102b are divided along a plane that traverses a longitudinal axis "X". When joined, the distal and proximal sections 102a, 102b define an upper cavity 106 therein in which electrical components, such as a circuit board 108 and a drive mechanism 110, are situated. An upper gasket 112 extends completely around a rim of the distal and proximal sections 102a, 102b and is interposed therebetween to seal the perimeter of the distal and proximal sections 102a, 102b such that the circuit board 108 and the drive mechanism 110 are protected during sterilization and/or cleaning procedures, such as autoclaving.

A lower cavity 114 (shown in phantom) is also defined within the housing 102. Electrical components, such as a circuit board 116 and a battery 118, are situated within the lower cavity 114. A door 120 is pivotally connected to the housing 102 for providing external access to the lower cavity 114. A lower gasket 122 is disposed around the door 120 to seal the lower cavity 114 and protect the circuit board 116 and the battery 118 during sterilization and/or cleaning procedures.

An aperture 124 is formed in an inner wall 126 separating the upper and lower cavities 106, 114 to provide a passage through which wires 128 may be passed to connect the electrical components (e.g., the circuit board 108) positioned within the upper cavity 106 with electrical components (e.g., the circuit board 116) positioned within the lower cavity 114. A gasket 130 is disposed within the aperture 124 thereby plugging or sealing the aperture 124 while allowing the wires 128 to pass therethrough. The gasket 130 establishes a fluid tight seal between the upper and lower cavities 106, 114 such that the electrical components in each cavity are protected during sterilization and/or cleaning procedures. Wires 128 are also passed between electrical components disposed within each of the upper and lower cavities 106, 114, such as between the circuit board 116 and the battery 118 disposed within the lower cavity 114, and the drive mechanism 110 and the drive connectors 132 (FIG. 3A) disposed within the upper cavity 106.

Figure 3A:
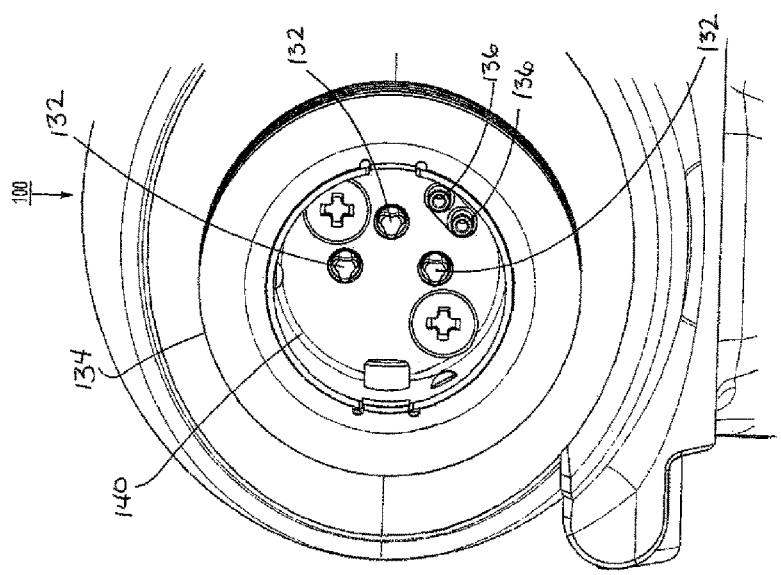

As illustrated in FIGS. 3A and 3B, in conjunction with FIGS. 1 and 2, the housing 102 includes a connecting portion 134 configured for receiving an adapter and/or end effector (not shown). The connecting portion 134 includes drive connectors 132 which couple with corresponding connector sleeves (not shown) of the mating adapter and/or end effector and are controlled by the drive mechanism 110.

The drive connectors 132 allow the surgical device 100 to selectively actuate different functions of an end effector, for example selective and independent opening and closing of a jaw assembly and/or driving of a stapling and/or cutting tool. The connecting portion 134 also includes electrical plugs 136 which couple with corresponding electrical plugs (not shown) of the mating adapter and/or end effector. The specific means of actuation and function of the adapters and/or end effectors are within the purview of those skilled in the art and may vary depending upon the application and use of the surgical device.

The drive connectors 132 are electrically connected to the drive mechanism 110 and the electrical plugs 136 are electrically connected to the circuit board 108 via wires 128. A wire 128 may be passed through a connector, such as a bulkhead connector 138, which forms, for example, an electrical contact with the drive connector 132 through a wall 140 to which the drive connectors 132 are mounted. Alternatively, wires 128 may be in direct electrical contact with an electrical component, such as the electric plug 126 positioned through the wall 140 without the use of a connector.

Figure 4:
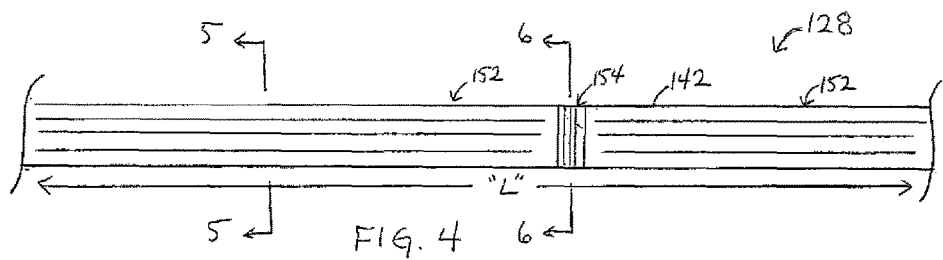
FIG. 4 is a side view of a wire in accordance with an embodiment of the present disclosure.
Figures 5, 6:
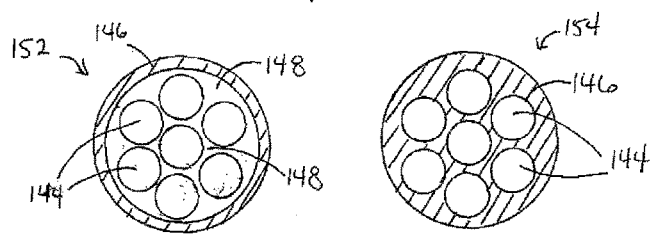
FIG. 5 is a cross-sectional view of the wire taken along line 5-5 of FIG. 4.
FIG. 6 is a cross-sectional view of the wire taken along line 6-6 of FIG. 4.

Referring now to FIGS. 4-6, each wire 128 includes an elongate flexible body 142 having a length "L" and one or more electrically conductive strands 144 enclosed within an insulation jacket 146. As used herein, the term "flexible" shall be understood to mean that the body 142 may bend and sustain repeated flexure without cracking, breaking, or otherwise compromising the integrity of the conductive strands 144 and insulation jacket 146. In embodiments, the wire 128 has a circular transverse cross-sectional profile extending uniformly along the length "L" of the body 142. It should be understood, however, that other cross-sectional profiles of the wire 128 are envisioned, such as oval, elliptical, etc. The cross-sectional profile of the wire 128 may be complementary in shape with an opening in a wall or connector of a surgical device to form a fluid tight, friction fit with the opening. In embodiments, a wire 128 having a circular cross-sectional profile forms a fluid tight fit with a circular opening in any of the inner wall 126, the gasket 130, the wall 140, and the connector 138 of the surgical device 100 of FIG. 1 when the wire 128 is passed therethrough.

The conductive strands 144 may be fabricated from any electrically conductive material, such as, for example, copper, aluminum, silver, and alloys thereof. The strands 144 may also include a protective coating, such as cadmium plating, to prevent corrosion of the wire 128. The insulation jacket 146 may be fabricated from any material capable of electrically insulating the strands 144, including, for example, polyethylene, polypropylene, polyvinyl chloride, copolymers and combinations thereof. It should be understood that the material of the strands 144 and jacket 146 are not particularly limited and are dictated by the design, usage, and desired properties of the wire 128.

As illustrated in FIG. 5, internal voids or spaces 148 are defined between the strands 144, and between the strands 144 and the inner surface 150 of the insulation jacket 146. In an embodiment, a majority of the wire 128 (FIG. 4) includes unsealed portions 152 in which the internal spaces 148 are open. As illustrated in FIG. 6, the wire 128 includes at least one sealed portion 154 at a point along the length of the wire 128. The sealed portion 150 is formed by filling the internal spaces 148 with a filler material 156 to prevent the passage of fluid through the wire 128. Depending upon the type and amount of filler material 156 used, the filler material 156 may cause the sealed portion 154 of the wire 128 to be stiffer than the unsealed portion 152 of the wire 128 which can limit the flexibility of the wire 128 and cause failure of the wire 128. As such, the sealed portion 154 may be positioned at select locations within the surgical device 100 (FIG. 1) where flexibility in the wire 128 is not critical, such as within the gasket 130 (FIG. 2) or the connector 138 (FIG. 3B).

It should be understood that the wire 128 may be internally sealed at one or more points along the length "L" of the wire 128. Multiple sealed portions 154, for example, can be placed within the wire 128 at any location along the length "L" of the wire 128 deemed appropriate by those skilled in the art. The sealed portions 154 may act as baffles along the length "L" of the wire 128 to inhibit transmission of fluid through the wire 128.

Figure 7:
FIG. 7 is a side view of a wire in accordance with another embodiment of the present disclosure.

In an embodiment, illustrated in FIG. 7, a wire 128a may include a first sealed portion 154a formed at a first end 158 of the wire 128a and a second sealed portion 154b formed at a second end 160 of the wire 128a thereby preventing the passage of fluid within any portion of the wire 128a. In such embodiments, the wire 128a may be utilized without a connector. Also, in such an embodiment, the length of the wire 128a between the sealed portions 154a, 154b may remain relatively more flexible than the sealed portions 154a, 154b, or stated differently, the flexibility will remain unchanged between the sealed portions 154a, 154b.

Figure 8:
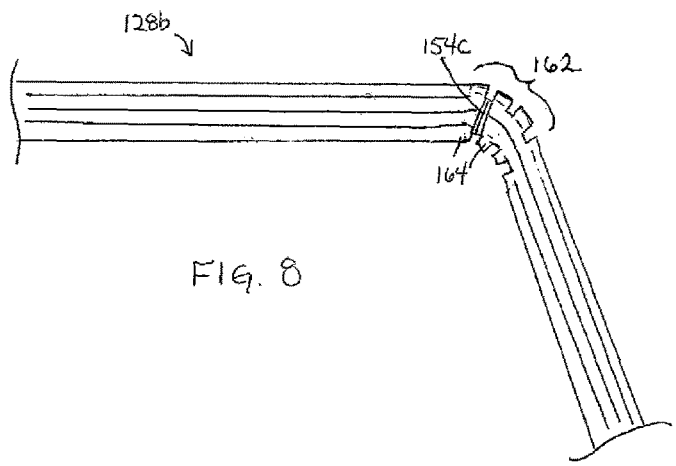
FIG. 8 is a side view of a wire in accordance with yet another embodiment of the present disclosure.

In an embodiment, shown in FIG. 8, a wire 128b may include at least one strain relief 162 formed in the insulation jacket 146. A sealed portion 154c may be formed between points 164 of the strain relief 162 so that the flexibility of the wire 128b is not otherwise affected by the stiffness that may be imparted to the sealed portion 154c.

The internal spaces 148 of the wire 128 may be filled with the filler material 156 in a variety of ways. In one embodiment, the material forming the insulation jacket 146 is thermally displaced into the internal spaces 148. In such embodiments, thermal energy may be selectively applied to a portion of the wire 128 so that the insulation jacket 146 melts into the internal spaces 148 in only the desired region to form the sealed portion 154. In another embodiment, the insulation jacket 146 is mechanically displaced, such as by crimping, into the internal spaces 148. In some embodiments, a combination of thermal and mechanical displacement may be utilized to form one or more sealed portions 154 in a wire 128.

In an alternate embodiment, the filler material 156 may be a sealant that is injected or otherwise positioned within the internal spaces 148. The sealant may be a hydrogel or a foam which expands within the internal spaces 148 of the wire 128. In some embodiments, the sealant may be coated on the strands 144 or the inner surface 150 of the insulation jacket 146 in, for example, a powder or particulate form, which may be activated upon exposure to moisture. In such embodiments, the sealed portion 154 may be formed within the wire 128 only upon exposure of a passing fluid within the wire 128, where the filler material 156 both prevents the transmission of the fluid through the wire 128 and absorbs the fluid disposed therein.

An outer surface 166 of the insulation jacket 146 may include a visual indicator to indicate proper sealing within the wire 128. In embodiments, a thermochromic coating may be applied to the outer surface 166 of the insulation jacket 146 so that upon application of thermal energy, as discussed above, the insulation jacket 146 will change color only at the location which has been heated to differentiate between the unsealed and sealed portions 152, 154 of the wire 128.

While the above description contains many specifics, these specifics should not be construed as limitations on the scope of the present disclosure, but merely as exemplifications of embodiments thereof. It is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Those skilled in the art will envision many other possible variations that are within the scope and spirit of the present disclosure.

What is claimed is:

1. A surgical instrument, comprising:
   a housing including a wire disposed therein, the wire including a first end connected to a first electrical component and a second end connected to a second electrical component, the wire having an elongate flexible body including:
   an insulation jacket defining an outer surface of the wire; and
   a plurality of electrically conductive strands disposed within the insulation jacket,
   wherein internal spaces defined between the insulation jacket and the plurality of electrically conductive strands are filled with a filler material at a sealed portion of the wire, the sealed portion positioned between two points of a strain relief of the wire, and each of the two points of the strain relief is a ridge defined in the insulation jacket.

2. The surgical instrument of claim 1, wherein a majority of a length of the wire is an unsealed portion wherein the internal spaces are open.

3. The surgical instrument of claim 1, wherein the wire extends through a gasket and the sealed portion is positioned within the gasket.

4. The surgical instrument of claim 1, wherein the wire includes two sealed portions.

5. The surgical instrument of claim 4, wherein the two sealed portions are disposed at the first and second ends of the wire.

6. The surgical instrument of claim 5, wherein at least one of the first or second ends is disposed within a connector.

7. The surgical instrument of claim 5, wherein at least one of the first or second ends is free of a connector and is in direct contact with its respective first or second electrical component.

8. The surgical instrument of claim 1, wherein the filler material is displaced material of the insulation jacket.

9. The surgical instrument of claim 1, wherein the filler material is a sealant.

10. The surgical instrument of claim 9, wherein the sealant is a hydrogel or a foam.

11. The surgical instrument of claim 1, wherein the outer surface of the insulation jacket includes a visual indicator to differentiate between the sealed portion and an unsealed portion wherein the internal spaces are open.

12. The surgical instrument of claim 1, wherein the housing includes a connecting portion configured for selective attachment of an adapter or an end effector, the housing configured to actuate the end effector.

13. The surgical instrument according to claim 1, wherein the outer surface of the insulation jacket is a continuous, uninterrupted surface.

14. A surgical instrument comprising:
a housing including a wire disposed therein, the wire including a first end connected to a first electrical component and a second end connected to a second electrical component, the wire having an elongate flexible body including:
- an insulation jacket defining an outer surface of the wire; and
- a plurality of electrically conductive strands disposed within the insulation jacket, wherein internal spaces defined between the insulation jacket and the plurality of electrically conductive strands are filled with a filler material at two sealed portions of the wire, the two sealed portions disposed at the first and second ends of the wire, at least one of the first or second ends disposed within a bulkhead connector.

15. The surgical instrument of claim 14, wherein the wire includes a strain relief and the sealed portion is positioned between two points of the strain relief.

16. The surgical instrument of claim 15, wherein each of the two points of the strain relief is a ridge defined in the insulation jacket.

17. The surgical instrument of claim 14, wherein a majority of a length of the wire is an unsealed portion wherein the internal spaces are open.

18. The surgical instrument of claim 14, wherein one of the first or second ends is free of a connector and is in direct contact with its respective first or second electrical component.

19. The surgical instrument of claim 14, wherein the filler material is displaced material of the insulation jacket.

20. The surgical instrument of claim 14, wherein the filler material is a sealant.

* * * * *